(12) United States Patent
Weeks et al.

(10) Patent No.: US 12,207,889 B2
(45) Date of Patent: Jan. 28, 2025

(54) ENDOSCOPE WITH PROCEDURE GUIDANCE

(71) Applicant: PacificMD Biotech, LLC, Henderson, NV (US)

(72) Inventors: Brian Hunter Weeks, Henderson, NV (US); Ashley Sikand, Las Vegas, NV (US); Jetmir Palushi, Irvine, CA (US)

(73) Assignee: PacificMD Biotech, LLC, Henderson, NV (US)

( * ) Notice: Subject to any disclaimer, the term of this patent is extended or adjusted under 35 U.S.C. 154(b) by 375 days.

(21) Appl. No.: 17/724,234

(22) Filed: Apr. 19, 2022

(65) Prior Publication Data
US 2022/0331014 A1    Oct. 20, 2022

Related U.S. Application Data

(60) Provisional application No. 63/176,455, filed on Apr. 19, 2021.

(51) Int. Cl.
*A61B 34/20* (2016.01)
*A61B 1/00* (2006.01)
*A61B 90/00* (2016.01)

(52) U.S. Cl.
CPC .......... *A61B 34/20* (2016.02); *A61B 1/00009* (2013.01); *A61B 1/0005* (2013.01); *A61B 90/39* (2016.02); *A61B 2034/2055* (2016.02); *A61B 2034/2065* (2016.02); *A61B 2090/3912* (2016.02)

(58) Field of Classification Search
CPC ... A61B 34/20; A61B 1/00009; A61B 1/0005; A61B 90/39; A61B 2034/2055; A61B 2034/2065; A61B 2090/3912; A61B 2018/00577; A61B 1/000096
See application file for complete search history.

(56) References Cited

U.S. PATENT DOCUMENTS

2016/0008083 A1*  1/2016  Kesten ............. A61B 5/062
                                                      600/424

* cited by examiner

*Primary Examiner* — Amelie R Davis

(57) ABSTRACT

An endoscope based system is configured to provide one or more procedure guidance features. The endoscope is paired with an image processing device that performs object detection and other analysis on captured images, and displays an interface to users that includes various visual guidance combined with endoscopic images. Interfaces displayed in different modes may indicate the location and extent of energy delivery tracked by the system, may guide placement of implant devices, may identify the location of nerves within tissue, and may provide step-by-step guidance for navigating the endoscope to certain anatomy. In some implementations, a removable and replaceable sheath may be coupled to the endoscope, and may enable one or more functional features of the endoscope while maintaining a sterile barrier. Sheaths may include an embedded memory that stores procedure configurations and procedure results.

20 Claims, 12 Drawing Sheets

ENDOSCOPE WITH PROCEDURE GUIDANCE

PRIORITY

This application claims priority to U.S. Provisional Patent Application 63/176,455, filed Apr. 19, 2021, and titled "Endoscope with Procedure Guidance," the entire disclosure of which is hereby incorporated by reference.

FIELD

The disclosed technology pertains to an endoscope system with automated analysis of anatomy and a procedure guidance interface.

BACKGROUND

Medical diagnosis is an important part of medical practice and may include a series of questions asked of a patient, physical examination or manipulation of the patient, collection of patient specimen samples, and use of instruments such as endoscopes and other diagnostic data collecting instruments. Each treatment that is provided to a patient may be contingent upon one or more prior diagnostic steps, and some diagnostic steps may themselves be contingent upon prior assessments. As a result, patients visiting a health care provider may be subjected to dozens of diagnostic steps over the course of identifying and treating a condition, many of which are diagnosed based on subjective determinations. As a result, accuracy of the diagnosis of the condition is very heavily dependent on the subjective skill of the particular surgeon, so results and accuracy can be varied.

With these frequent diagnostic steps, factors such as time, cost, accurate diagnosis, and patient comfort become very important. A diagnostic or therapeutic procedure might include physical manipulation and a series of questions during a 5-10 minute interview, or within a magnetic resonance imaging scan ("MRI") or Computed Tomography (CT) for the same procedure might require an hour or more where the patient is immobilized and isolated within the close confines of an MRI or CT machine. In addition the use of MRI or CT machines to precisely diagnose certain treatments that endoscopic systems are not able to detect currently, exposes the patient and staff to potential health hazards such as cause of cancer.

In addition, for ear, nose, and throat ("ENT") treatment, diagnosing a treatable condition can be difficult due to the location and inability to directly view or access some anatomy related to ENT diagnosis. For example, while an otoscope may be used to quickly assess a patient for an ear infection, assessment of a patient for an obstruction of the nasal airways may require a computerized tomography scan ("CT"), MRI, or other complex, costly, inaccurate, skill-dependent and time-consuming imaging procedures. While such imaging procedures are important and useful for medical professionals, the results are often meaningless or confusing to patients since they are computer generated images based upon various signal feedback rather than direct imaging of the patient anatomy. Furthermore, the use of the currently diagnostic systems such as CT and MRI scanners, do not allow the doctor to direct the patient to perform certain tasks, such as for example breathing in and out, to detect the state of the disease progression based on the anatomy changes which is the case for airflow obstruction.

What is needed, therefore, is an improved system for providing information usable by medical professionals and patients to diagnose and understand certain anatomical characteristics.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

Figure 1:
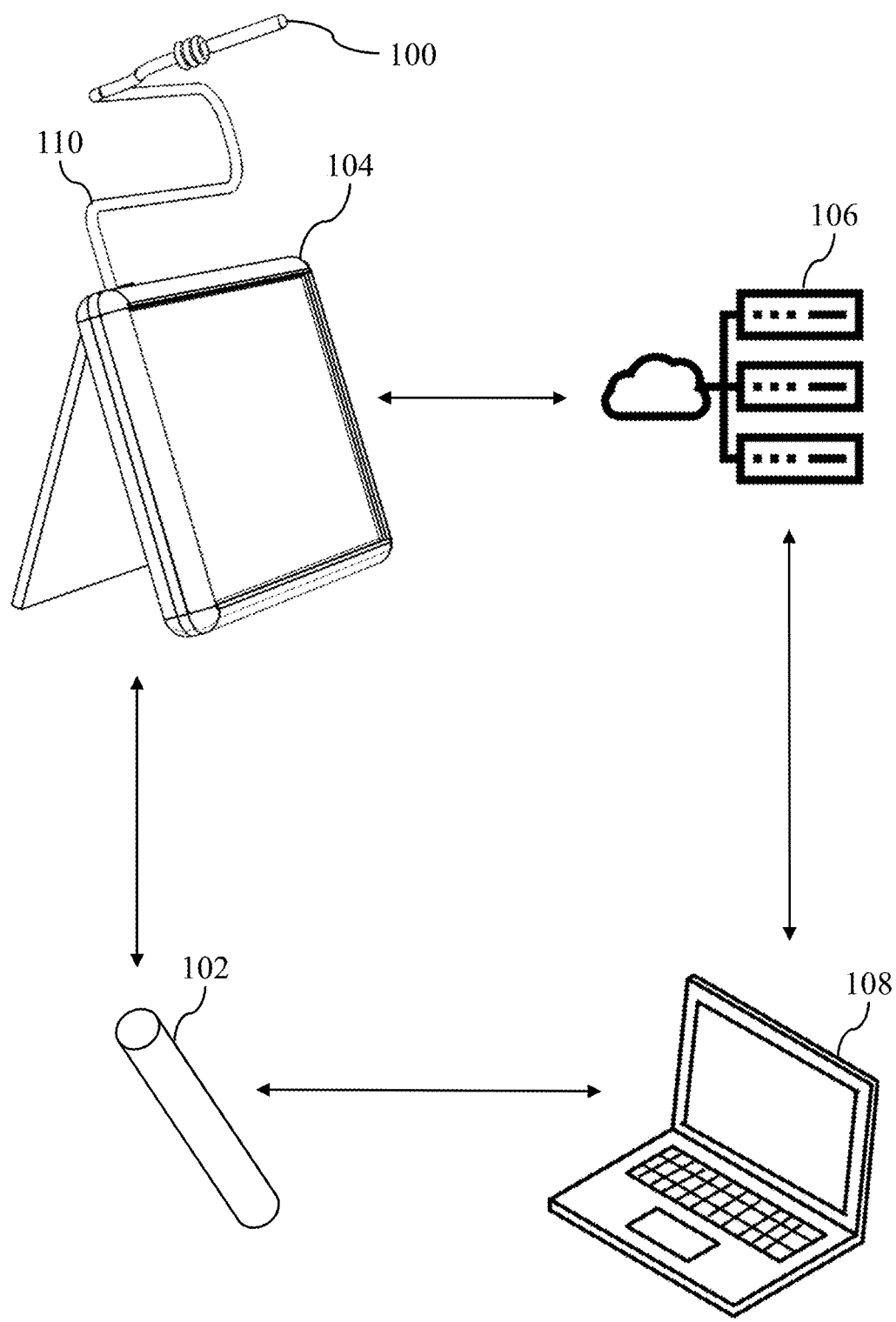
FIG. 1 is a schematic diagram of an exemplary system configured to provide medical imaging and/or treatment.

The inventors have conceived of novel technology that, for the purpose of illustration, is disclosed herein as applied in the context of an endoscope and functional endoscope sheath. While the disclosed applications of the inventors' technology satisfy a long-felt but unmet need in the art of endoscope sheaths, it should be understood that the inventors' technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

Implementations of the disclosed technology may utilize an endoscope to provide automated detection and identification of anatomy and other points of interest within images captured by the endoscope, and may use such images and associated identifications to provide software interfaces that guide a surgeon through one or more procedures by providing enhanced visualizations, instructions, and information related to the procedure site. Analysis of images and identification of anatomy may be performed using combinations of expert systems, trained artificial intelligence systems, and manual user inputs. The endoscope system may be configured to provide one or more different types of procedure guidance.

As one example, the system may be configured to provide an interface for energy tracking during use of an ablation instrument or other surgical instrument that provides energy to affect tissues. The interface may identify locations where energy has been delivered (e.g., or a tool of any type has been activated), the magnitude of delivery, a time period of delivery, and the visually apparent effects of delivery (e.g., before-and-after image comparisons). As another example, the system may provide an interface for guiding placement of an implant, including estimating instrument tip position and orientation, incision locations, implant depth, and other characteristics. As another example, the system may provide an interface for identifying the positions and depth of nerves or other anatomy that is present within tissue based upon exterior imaging of the tissue, and may provide procedural guidance for interacting with the identified nerves (e.g., during energy delivery to affect the nerves). As another example, the system may provide an interface for identifying certain key anatomical characteristics based upon imaging of surrounding anatomy, such as identifying the location of the opening of a Eustachian tube, and providing guidance for an instrument being navigated to the tube.

Some implementations of the disclosed technology may include a disposable sheath that includes one or several functional characteristics, and an endoscope or other instrument to which the sheath may be coupled. During use, the sheath is the only part of the medical instrument that contacts the patient, and so the medical instrument can be ready for a subsequent use by removing and disposing of a used sheath, and then opening/unsealing and installing a new sterile sheath.

In addition to providing a low cost and easily replaceable sterile shield between patients and reusable medical instrument such as an endoscope or tissue ablation tool, implementations of the disclosed technology may include varying combinations of functional features that are enabled by a particular sheath and/or are encapsulated by the sheath to maintain their sterility, which may include optical components, use tracking and diagnostic features, procedure software auto-configuration, fluid and/or drug delivery, tissue ablation through electric or sonic energy delivery, delivery of sinuplasty balloon or other medical device, structure, or material, and other features that will be described in more detail below. Features and functions of the sheath may include some or all of those described in U.S. patent application Ser. No. 17/702,628, filed Mar. 23, 2022, and titled "Endoscope and Endoscope Sheath with Diagnostic and Therapeutic Interfaces," the entire disclosure of which is hereby incorporated by reference herein.

Turning now to the figures, FIG. 1 shows a schematic diagram of a system configured to provide medical imaging and/or treatment. The system includes a medical instrument in the form of an endoscope (100), which may be flexible, semi-flexible or rigid that is coupled to an image processor (104) by a cable (110), which may be a flexible or semi-flexible multi-channel cable that allows for the exchange of power and data between the image processor (104) and the endoscope (100). An endoscope sheath (102) is configured to couple with the endoscope (100) to provide a sterile barrier between the patient and endoscope (100). The endoscope sheath (102) may contain a memory device, microprocessor, and communication device (e.g., a wireless or wired data connection) allowing for the exchange of data between the endoscope sheath (102) and a coupled endoscope (100), and also allowing for communication between the endoscope sheath (102) and other devices such as a user device (108).

The image processor (104) and user device (108) may each be in communication with a remote server (106), and may exchange diagnostic information, troubleshooting information, software configurations, software applications, and other information. Functions performed by the remote server (106), image processor (104), and user device (108) may include some or all of those described in U.S. patent application Ser. No. 17/669,952, filed Feb. 11, 2022, and titled "Systems and Methods for Endoscopic Imaging and Analysis," the entire disclosure of which is hereby incorporated by reference herein. Diagnostic information, troubleshooting information, and other information also can be exchanged via the sheath memory, where this information is stored in the case of such an event occurring, and the sheath is sent back to the manufacturer where they can download this information for further analysis.

Information stored on a memory of the endoscope sheath (102) may include, for example, procedure configurations and other software configurations, serial numbers or other unique identifying data, information usable with the image processor (104) or remote server (106) to authenticate, validate, or otherwise provide access to or enable features of one or more of those devices. The endoscope sheath (102) may be preconfigured with a set of initial information, and may be configured to receive and store additional information during use with the endoscope (100), which may include diagnostic information from the endoscope (100) and/or image processor (104), error codes, performance characteristics, performance results, captured images, captured video sequences, results of image analysis, results of analysis for anatomical characteristics, and other information. The sheath memory also store data usable to update or further optimize the algorithm residing within the image processor (104) (e.g., updated software or image analysis datasets may be delivered to the image processor (104) via the sheath memory).

As one example, the image processor (104) and/or remote server (106) may be configured to provide automated image analysis of image data captured by the endoscope (100) to aid in identifying target tissues, anatomical structures, or medical concerns that may be apparent in captured image data. This image analysis feature may only be usable when an activation key or other data is received from the endoscope sheath (102) upon coupling with the endoscope (100), and then provided to the image processor (104) and/or remote server (106) where the activation key is validated or otherwise authenticated. After receiving a valid activation key from the endoscope (100), the system may provide automated image analysis or other features to that endoscope (100) for a period of time, or during a particular usage session. In some implementations, the activation key may be limited to a single use or a small number of uses, such that subsequent uses of the endoscope sheath (102) with the endoscope (100) may be denied use of the automated image analysis feature.

Such limitations may be enforced by data stored on the endoscope sheath (102), image processor (104), or remote server (106) indicating that the particular activation key has already been used or is otherwise expired or invalid, which data may be written to those devices after a prior use of the activation key. As another example, the activation key may be stored as a read-once portion of memory on a memory chip of the endoscope sheath (102), such that the data is no longer stored or available on the chip after the first time it is accessed. As another example, the activation key may be stored on a memory chip that is damaged or destroyed by the act of decoupling the endoscope sheath (102) from the endoscope (100), or locking the endoscope sheath (102) to the endoscope (100).

In some implementations, the endoscope sheath (102) may receive and store on a memory chip operational details from a procedure performed with the endoscope (100), which may include results of image analysis, error codes, images and video, and other information as has been described. Since the endoscope sheath (102) is removable and replaceable, it may be provided to a patient, medical surgeon, or technical support personnel after a procedure where such party desires access to information written to the memory chip as a result of the procedure. Such information may be accessed by coupling the endoscope sheath (102) to the user device (108) or another device and copying the desired information from the memory chip. Such coupling may be, for example, wireless (e.g., Bluetooth, NFC, RFID), or may be a direct coupling (e.g., USB, or other direct data connection such as a proprietary connection that couples to an adapter or dongle capable of USB connection).

In this manner, patients may retain images and/or analysis results from a procedure for their own use, surgeons may retain the same for further review, diagnosis, or treatment, and technical support personnel may access and review error codes or performance data usable to address errors and improve the system. Information stored on the endoscope sheath (102) may be encrypted and/or otherwise protected from casual access. In this manner, sensitive and proprietary information may be securely and readily exchanged by physical exchange of the endoscope sheath (102), which may alleviate concerns over cloud-based transmission and storage of the information, or the potential for loss of data when the procedure is performed in an "offline" setting where such information cannot be readily transmitted to the remote server (106) or another location.

Another example of information stored on one or more memory chips of the endoscope sheath (102) include specific procedural information, such that a particular sheath may be configured to be used for a particular procedure. As an example, one endoscope sheath (102) may be configured for analysis of a nasal obstructive airflow, and when coupled to the endoscope (102) and in communication with the image processor (104), the stored information may be used to automatically initiate the software of the image processor (104) for this particular disease (e.g., the graphical user interface, device settings, software settings, and automated image analysis type may be determined and loaded automatically based on the received information once the endoscope sheath (102) is attached).

The image processor (104) may be, for example, a computer, tablet device, or other computing device having capabilities such as a display, touch sensitive surface, buttons, processor, memory, communication devices (e.g., Wi-Fi, Bluetooth, USB, Ethernet, or other wireless or wired data interface), and other features. The image processor (104) may be configured with software allowing for offline image capture and image analysis, or may be configured to access such software at the remote server (106) or another location when connected to the internet via a cellular network or other channel. The image processor (104) may also be configured with software for managing the performance of the endoscope (100), and may adjust and control image resolution, framerate, and other characteristics of image capture, as well as the output and characteristics of light provided by LEDs, laser light emitters, or other devices of the endoscope (100). As an example, the image processor (104) may automatically adjust the output of one or more LED lights at a distal tip of the endoscope (100) based upon captured images, in order to automatically adjust the level of light in real-time during imaging.

The user device (108) may be, for example, a computer, tablet device, smartphone, or other computing device capable of exchanging, manipulating, and storing data, and including a processor, memory, storage device, communication device, and other components. The remote server (106) may include one or more physical servers, virtual servers, cloud servers, remote servers, or other computing environments, with each server having processors, memory devices, communication devices, and other components as may be required to exchange, manipulate, and store data.

While the system of FIG. 1 shows the endoscope sheath (102), endoscope (100), and image processor (104), it should be understood that other medical instruments and related devices may be used in varying implementations. As an example, a sheath configured for use with a balloon dilation driver may have some or all of the features described in the context of FIG. 1, but may be coupled to an inflation (e.g., fluid or gas) source or other device instead of the imaging processor (104). As another example, a sheath configured for use with a sonic ablation device may be coupled to a power source or sonic pulse generator instead of the imaging processor (104). As further example, each of the above examples may also include an endoscopic tip usable in conjunction with the balloon dilation feature or tissue ablation feature, and so may include the image processor (104) in addition to sources for inflation, sonic pulse generation, irrigation, vacuum, or other features.

Figure 2:
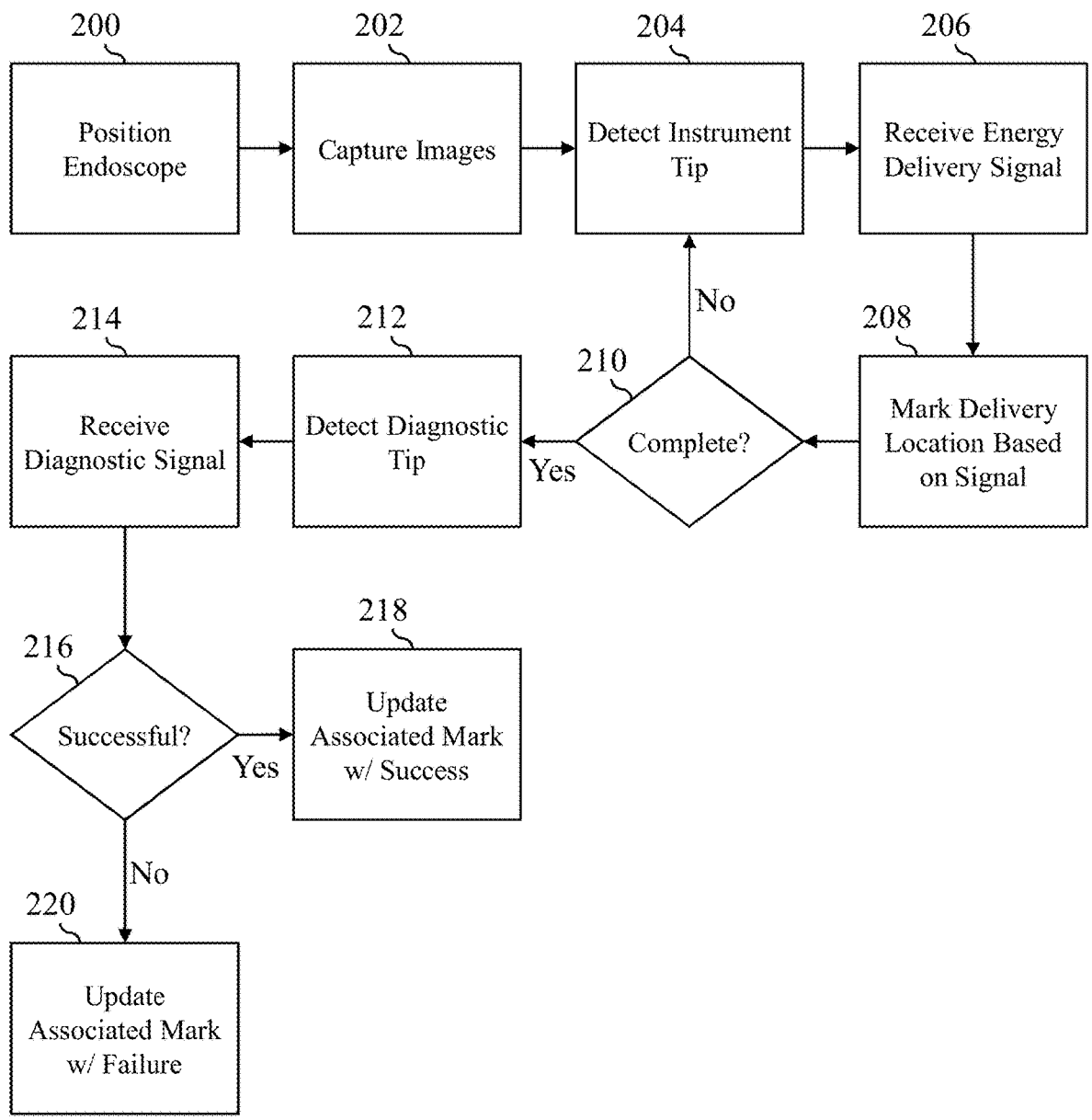
FIG. 2 is a flowchart of an exemplary set of steps that may be performed to provide procedure guidance during use of a surgical instrument.

The procedure guidance techniques described in the context of FIG. 2 and elsewhere herein may advantageously utilize an endoscope both for its conventional purpose (e.g., providing real-time visuals of an anatomy that is obscured or otherwise difficult to directly view), as well as for capturing images that may be analyzed using object recognition and other machine vision techniques, which may be in the form of an artificial intelligence system using machine learning or other techniques, an expert system configured to detect certain visual characteristics, other image analysis techniques, or combinations thereof. This allows endoscopic imaging to be enhanced in near real-time to provide additional information and guidance during a procedure, and may be used in addition to or as a replacement for other image guided surgery techniques. This may advantageously allow a surgeon to provide diagnostics and/or treatments to patients in settings where stationary capital equipment is not available or not reasonable, as it allows for enhanced visualization of a procedure site during a procedure without requiring pre-operative imaging by an MRI machine, CT scanner, or other imaging device, and without requiring the use of a magnetic field generation and position tracking suite, or other surgical tracking systems.

Turning now to FIG. 2, that figure shows a flowchart of an exemplary set of steps that may be performed to provide procedure guidance during use of a surgical instrument such as a tissue ablation instrument that delivers electric, sonic, thermal, or other energy types to treat and affect contacted and/or proximal tissues. Software configured to perform the steps of FIG. 2 may be configured on one or more of the endoscope (100), the image processor (104), or the remote server (106), and may be selectively activated by a user or may operate continuously during use of the endoscope (100). The endoscope (100) may be positioned (200) at the procedure site, which may include navigating the endoscope (100) to a position within the patient, and may also include use of a sheath (102) such as that described above. Images may be captured (202) by the endoscope during navigation, upon arrival at the procedure site, or both.

Figure 3A:
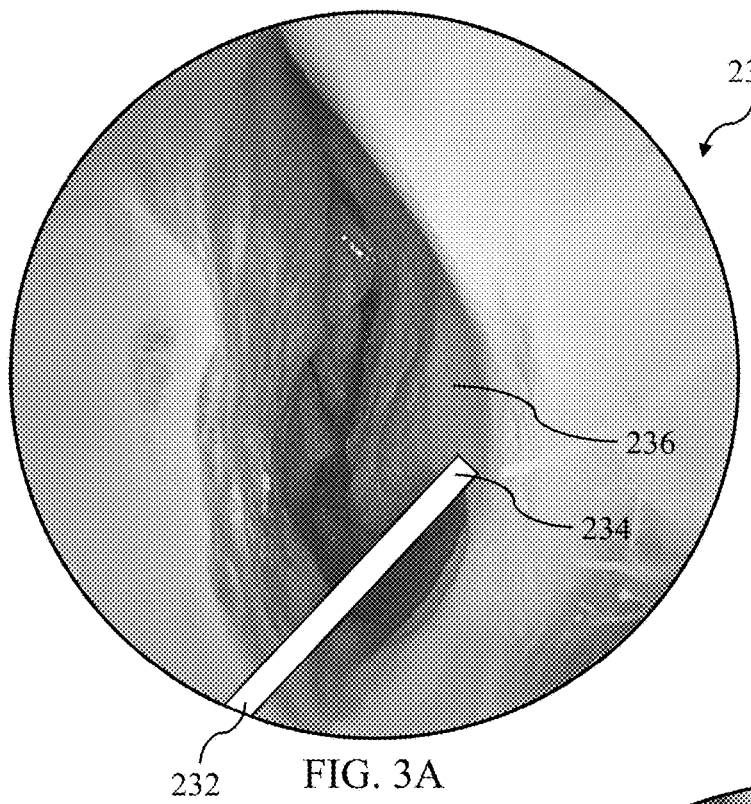
FIG. 3A-3D show exemplary interfaces that may be provided during procedure guidance such as that described in FIG. 2.

FIGS. 3A-3D each show exemplary interfaces that may be provided based in part upon captured images. FIG. 3A shows an interface (230) that may be displayed (e.g., on the image processor (104) or another device). The interface (230) shows an image captured (202) of the nasal cavity, with the field-of-view directed deeper into the nasal cavity. A distal end of a surgical instrument (232) is shown within the image, also having been navigated to the procedure site. The surgical instrument (232) may be of any type with an operative end effector usable to provide a treatment, and may be, for example an ablation instrument that includes an ablation contact (234) that delivers energy to contacted or proximal tissues. In FIG. 3A, the surgical instrument (232) is positioned near the turbinate (236).

Returning to FIG. 2, the system may detect an instrument tip within the captured images, such as the ablation contact (234), using an image recognition, object detection, or other machine vision feature, and may continuously track the detected (204) tip as subsequent images are captured. Analysis of images via such a feature may also include segmentation of the two dimensional image to estimate the depth of certain portions of the image, or may include other depth determination techniques which may include projection of laser focal point(s), projection of light patterns, or other optical projections which may be indicative of the scale and/or depth of portions of the image. In some implementations, the system may overlay a visual indicator upon the instrument tip which may display via the interface (230), and which may indicate to a user the accuracy of detection (204), and may provide the user an opportunity to re-map or re-assign the instrument tip (e.g., by clicking and dragging, touching and dragging, or otherwise interacting with the interface (230) to adjust the placement of the tip).

The system may receive (206) an energy delivery signal indicating that a feature of the surgical instrument (232) has been activated to delivery energy to tissue via the ablation contact (234). The energy delivery signal may be received (206) from the surgical instrument (232) and/or an attached surgical generator via a wireless or wired communication channel (e.g., Wi-Fi, Bluetooth, USB) between the surgical instrument system and the image processor (104) or another device of the endoscope system, or may be received (206) based upon detection of electric power, an electric field, a signal, or another characteristic of the surgical instrument. As an example, this may include an inline or proximal current detection device that is configured to detect electrical draw by the surgical instrument. The received (206) energy delivery signal may include, or may be indicative of an occurrence of energy delivery, a time period of the energy delivery, a magnitude of the energy delivery, and other information. As an example, a received (206) energy delivery signal may include (e.g., if an encoded transmission of data), or may indicate (e.g., based upon an interpretation of measured current draw) that an energy delivery has occurred lasting 30 seconds, and delivering 1.5 kJ of energy.

Figure 3B:
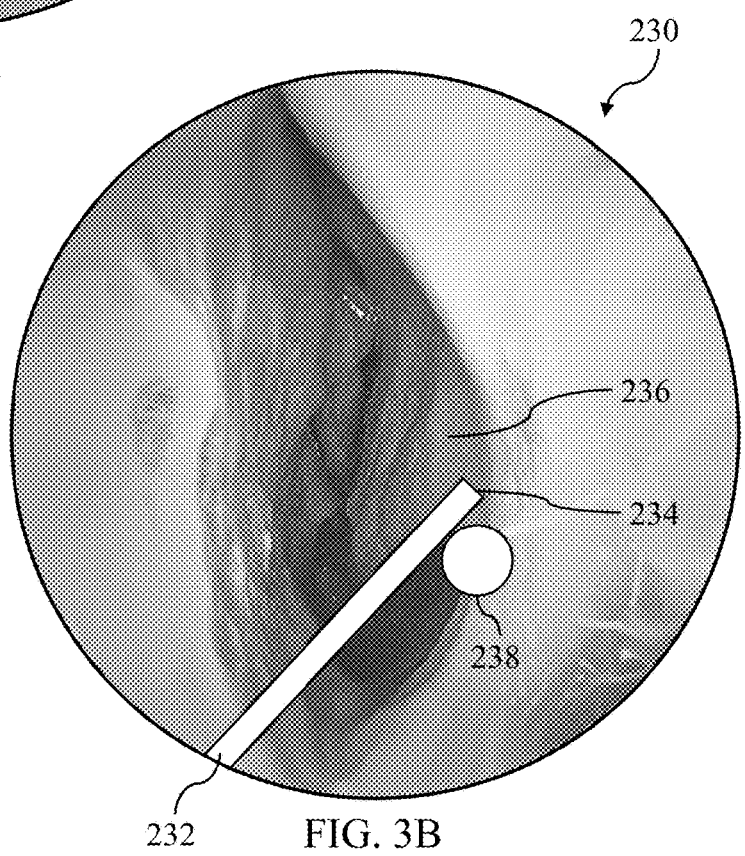

Based upon the received (206) energy delivery signal, the system may mark (208) the location of the ablation contact (234) within the captured images to indicate the occurrence of energy delivery, such that when the surgical instrument (232) is repositioned the energy delivery location remains marked, as depicted in the interface (230) of FIG. 3B. In that figure, it can be seen that the ablation contact (234) has been repositioned to a new location along the turbinate (236), and an energy delivery marker (238) remains at the original position of FIG. 3A. The energy delivery marker (238) may have varying shapes, sizes, colors, or other visual characteristics, and may include numeric or textual information, and in some implementations may be interacted with to view additional or different information. As an example, the size or color of the marker (238) may be determined based upon a length of ablation time, or a total energy delivered during ablation, or the size or color may be determined only based upon the total energy delivered, with the length of delivery being displayed when a user interacts with the marker (230) via the interface (230) (e.g., by touching the marker on a touchscreen, selecting the marker with a mouse cursor, etc.).

Placement of the marker (238), and other guidance features related to tracking the ablation contact (234), or tracking the distal tip or end effector of a surgical instrument more generally, may be performed based on the particular procedure being performed (e.g., the endoscope may be configured to support guidance for different procedure types, and so may be pre-configured for certain behavior for each procedure type), and the particular procedure event detected during procedure guidance (e.g., each procedure type may be associated with one or more detectable events). Procedure events may be monitored for and detected based on received procedure data as disclosed herein, and may include, for example, receiving a signal indicative of a surgeon input (e.g., pressing a button of the surgical instrument, a voice command input, an input to a software application etc.), receiving a signal indicative of a use of the surgical instrument (e.g., from a sensor or other device indicating power delivery or electrical draw during ablation, feedback from a diagnostic step or test such as a tissue impedance measurement), or a signal based on image data (e.g., a result of machine vision analysis based on captured image data and indicating the occurrence of power delivery, tissue ablation, or placement of a surgical implant or other device at an anatomical site).

As will be apparent to those skilled in the art based on this disclosure, the marker (238) and other markers, indicators, and event overlays described herein may be associated with underling image data as an overlay that may be displayed as part of a combined physical/virtual interface (e.g., such as shown in FIGS. 3A-3D).

The relative scale and position of such event overlays correspond to the position to which they are anchored or placed (e.g., upon or proximate to a particular patient anatomy), and so may remain fixed to that original position even where the endoscope view changes (e.g., due to the endoscope rotating, advancing, withdrawing, or otherwise changing its perspective from that when the event overlay was first positioned). In such an implementation and with reference to the interface (230) shown in FIG. 3C, the size of markers (238, 240, 242, 244) may increase as the endoscope is advanced into the nasal canal, or may decrease as the endoscope is withdraw from the nasal canal. Similarly, if the endoscope is rotated, the position of the markers (238, 240, 242, 244) may similarly rotate to maintain their original position relative to the anatomy or other structure at which they were placed. Similarly, if the rolls, pitch, or yaw of the endoscope is changed, the position of the overlaid markers (238, 240, 242, 244) may be adjusted to maintain their original position relative to the anatomy or other structure at which they were placed. Changes to position and scale of event overlays as a result of repositioning the endoscopic view may be performed based upon some or all of approximation of the two dimensional image data and tracked distal tip into a three dimensional coordinate systems (e.g., such as described below), relative perspective changes based upon sensor data from accelerometer sensors, gyroscopic sensors, tri-axis sensors, or other surgical instrument tracking systems (e.g., indicative of true position within a tracked three dimensional coordinate system, o r The procedure may continue until complete (210), with the instrument tip being continuously detected (204) at each energy delivery location so that the new location can be marked (208) based upon the received (206) energy delivery signal as has been described. Detection (204) of the instrument tip may include detection in a two dimensional x/y coordinate system (e.g., x and y position of the tip within the image), may include detection in a three dimensional x/y/z/coordinate system (e.g., both x/y position within the image, as well as the distance at which the tip is located from the endoscope perspective), and may include detection of the orientation of the distal tip within three dimensional space (e.g., with up to six degrees of freedom, which may indicate the orientation of a shaft or other portion of the surgical instrument).

Figure 3C:
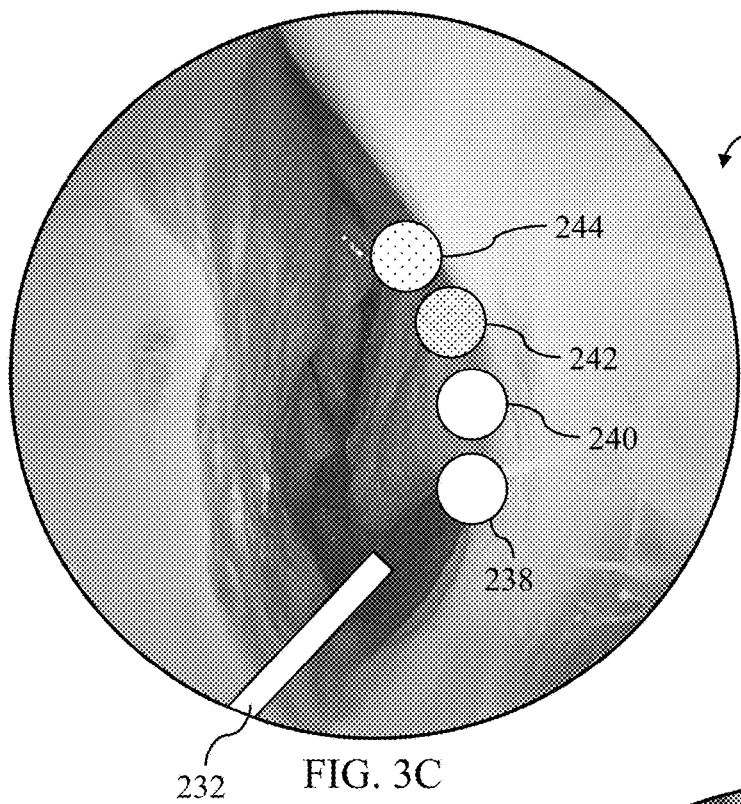

FIG. 3C shows the interface (230) after energy has been delivered at additional locations. A marker (238) and a marker (240) are visually similar, indicating similar characteristics of the energy delivery. A marker (242) includes a distinct pattern or color, indicating a high level of energy delivery, while a marker (244) includes a different distinct pattern or color, indicating a moderate level of energy delivery. The relationship between energy delivery and visual appearance may be pre-configured by a manufacturer or provider of the system, may be manually configured by a user of the system, or may be automatically determined in part based upon a particular procedure (e.g., the energy delivered during "high" ablation during a tumor treatment procedure may be different than the energy delivered during "high" ablation during a nerve treatment procedure).

Returning to FIG. 2, once ablation is complete (210) the system may be placed into an ablation diagnostic mode whereby the surgical instrument (232) may be swapped for a diagnostic instrument, or may be operated in a diagnostic mode, in order to measure the effectiveness of the energy delivery. The system may detect (212) the position of a diagnostic instrument tip within the captured (202) images, and may track and/or mark the location of the diagnostic tip within the images as they are displaced via the interface (230), as has been described. The system may then receive (214) a diagnostic signal that includes, or that is indicative of, a diagnostic measurement of tissue with the diagnostic instrument. The diagnostic signal (214) may be received in varying ways, as described above in the context of receiving (206) the energy delivery signal.

The diagnostic signal may include or be indicative of information describing the diagnostic test, and, for example, may describe a measured tissue impedance to an electrical stimulation or nerve reception of a stimulation, or may instead indicate whether the ablation was successful or not based upon such information. As an example, in some implementations the image processor (104) or another device of the system may receive raw impedance measurements and may determine whether ablation was a success based on comparison to a preconfigured table of expected impedance measurements or other dataset, while in other implementations the diagnostic instrument may instead make such a determination and indicate by a Boolean value or other value that ablation was successful.

Figure 3D:
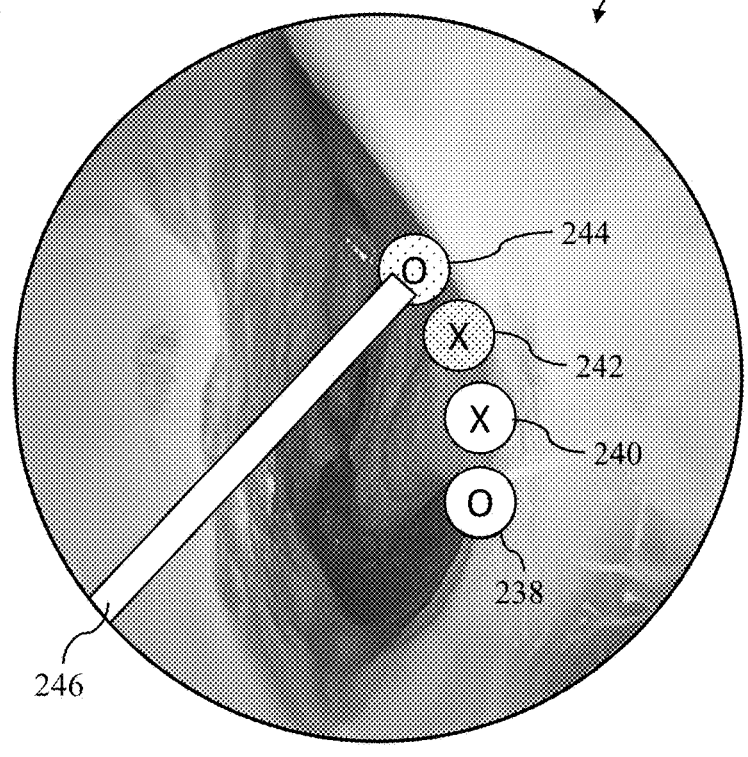

When a diagnostic signal is received (214) indicating successful ablation (216), the system may update a marker at which the diagnostic tip is located at the time of the diagnostic measurement to indicate a successful ablation, and may display the updated marker via the interface (230). Where the diagnostic signal does not indicate success (216), the system may update the marker at which the diagnostic tip is located to indicate a failed ablation, and may display the updated marker via the interface (230). As with prior examples, updated markers may include visually distinct characteristics, or may display diagnostic information when interacted with, to reflect whether they represent a successful or unsuccessful ablation. As an example, FIG. 3D shows the interface (230) following the use of a diagnostic instrument (246) on tissue located at each of the markers (238-244). Markers associated with a successful ablation have been marked with an "O", while markers associated with a failed ablation have been marked with an "X". Using this interface (230), the physician may repeat the ablation procedure at the same or different locations, perform further diagnostics, or otherwise, and in all cases the interface (230) may be updated to reflect the changes in tracked energy delivery (e.g., the marker (240) may change in pattern or color when more energy delivery signals are received at that location, or may change to an "O" when a subsequent diagnostic signal received at that location indicates a successful ablation).

Varying implementations of the disclosed system may support one or more different types of procedure guidance, and particular types of procedure guidance may be selected and/or enabled based upon user input, based upon pre-configured characteristics present in a sheath memory chip coupled to the endoscope, or in other ways. As an example of another type of procedure guidance that may be performed with the system, FIG. 4 shows a flowchart of an exemplary set of steps that may be performed to provide procedure guidance during placement of an implant, while FIG. 5 shows an example of an implant (336) and implant tool (330) usable with the steps of FIG. 4 to deploy a stabilizing implant within the nasal wall to prevent nasal collapse.

The implant tool (330) includes a shaft (332) that may include a sharpened or needle tip to enable the shaft (332) to penetrate into tissue of the nasal wall. The shaft itself (332) contains the implant (336) within a hollow interior, and the implant may include one or more flexible and/or gripping features that are retracted or otherwise non-operative while inside the shaft (332), but that deploy and/or expand once the implant (336) is deployed from the shaft (332). Once the shaft (332) is positioned within the nasal wall at a depth that allows for full deployment of the implant (336), a control (334) may be operated to retract the exterior cylinder of the shaft (332), leaving the implant (336) that was contained within the shaft's hollow interior at the deployment location.

Conventional approaches to such a procedure include marking the exterior of nose above the position where the implant is desired, and insertion of the shaft (332) into the nasal wall via the interior of the nasal canal, while its depth of insertion estimated by viewing and/or manually manipulating the exterior of the nose to feel for the shaft's (332) presence relative to the marking.

Figure 4:
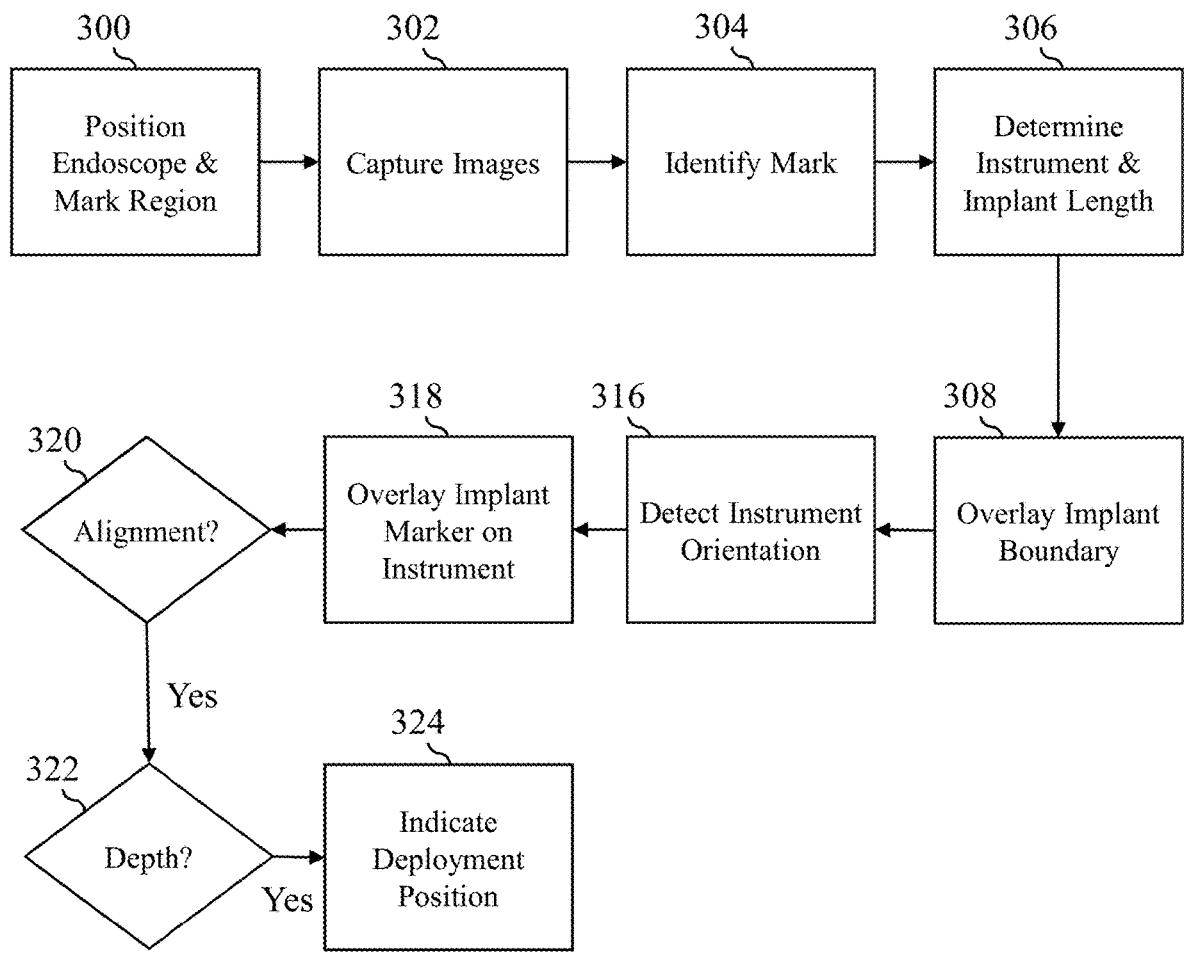
FIG. 4 is a flowchart of an exemplary set of steps that may be performed to provide procedure guidance during placement of an implant.
Figure 5:
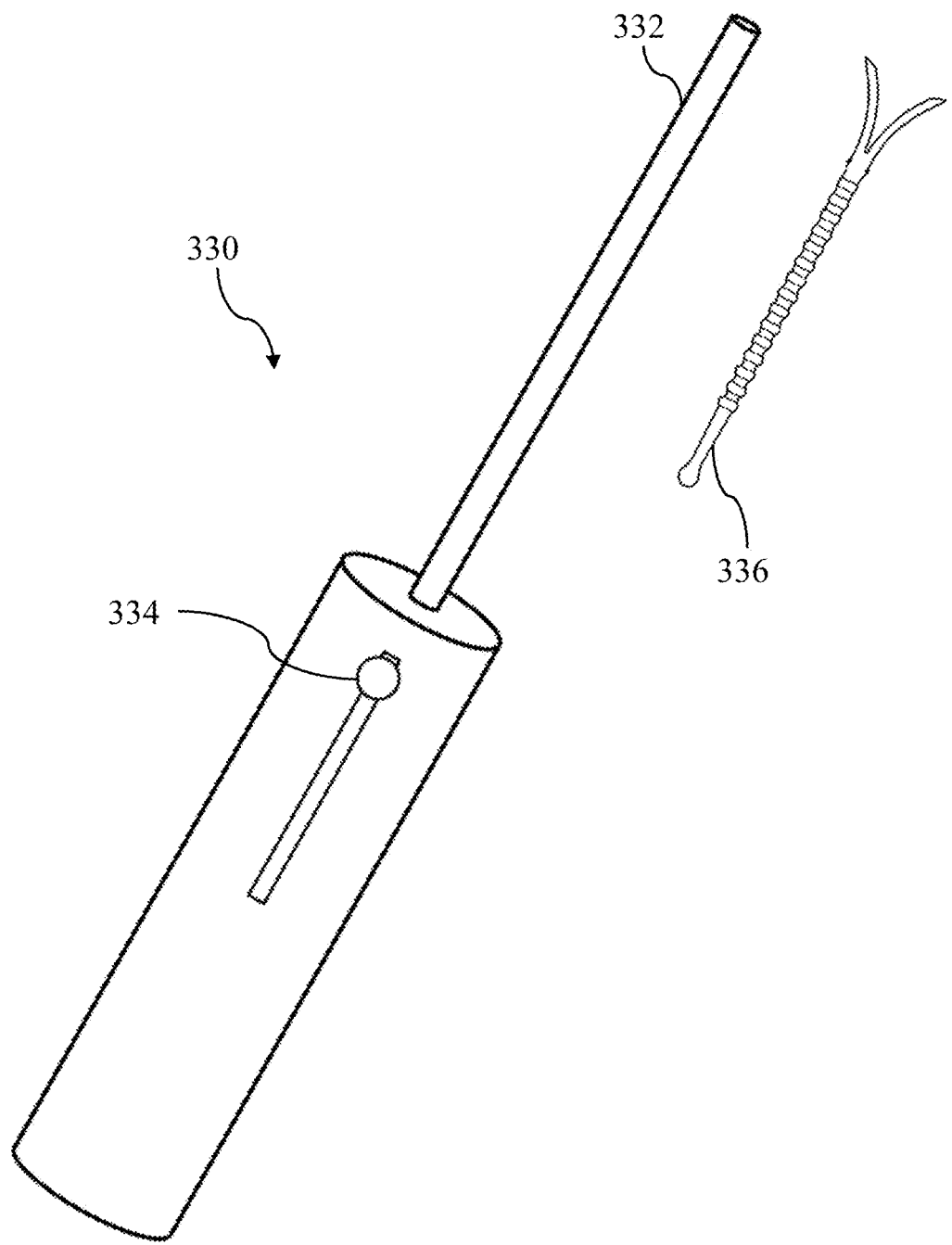
FIG. 5 is a perspective view of an exemplary implant tool and implant usable with the steps of FIG. 4.
Figure 6A:
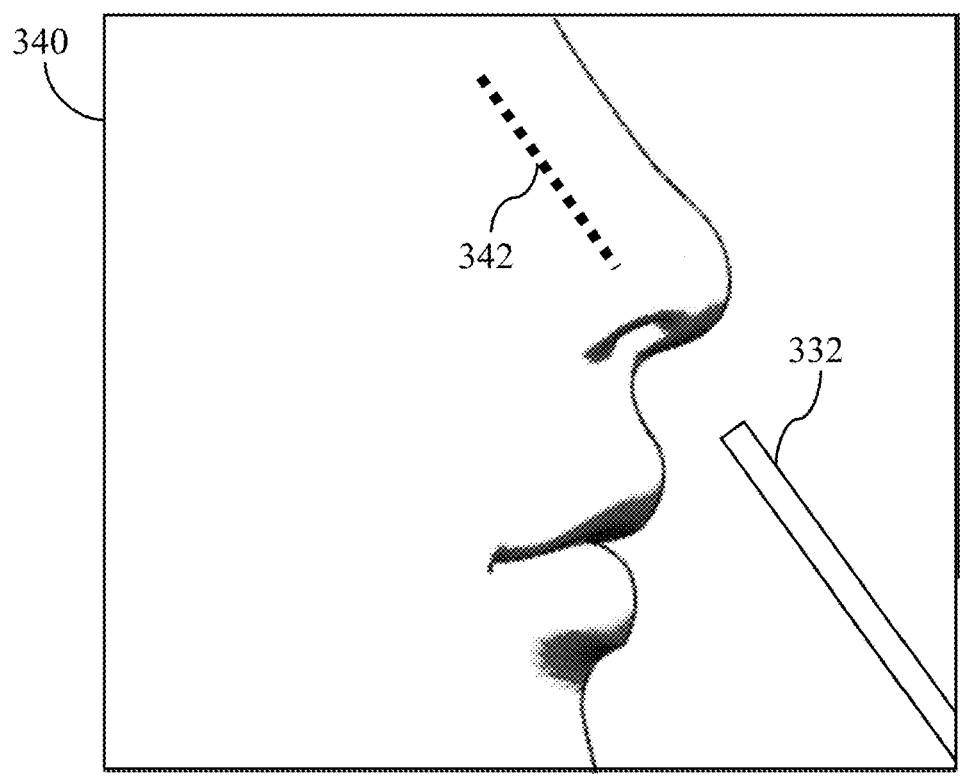
FIG. 6A-6D show exemplary interfaces that may be provided during procedure guidance such as that described in FIG. 4.

During procedure guidance as described in the steps of FIG. 4, the surgeon may position (300) the endoscope (100) and mark the region where the implant is to be deployed. In some instances, this may include positioning the endoscope (100) with an exterior view of the nose (e.g., such as depicted in FIG. 6A) and physically marking the nose with a visual guide (e.g., a sticker or colored marker).

Figure 6B:
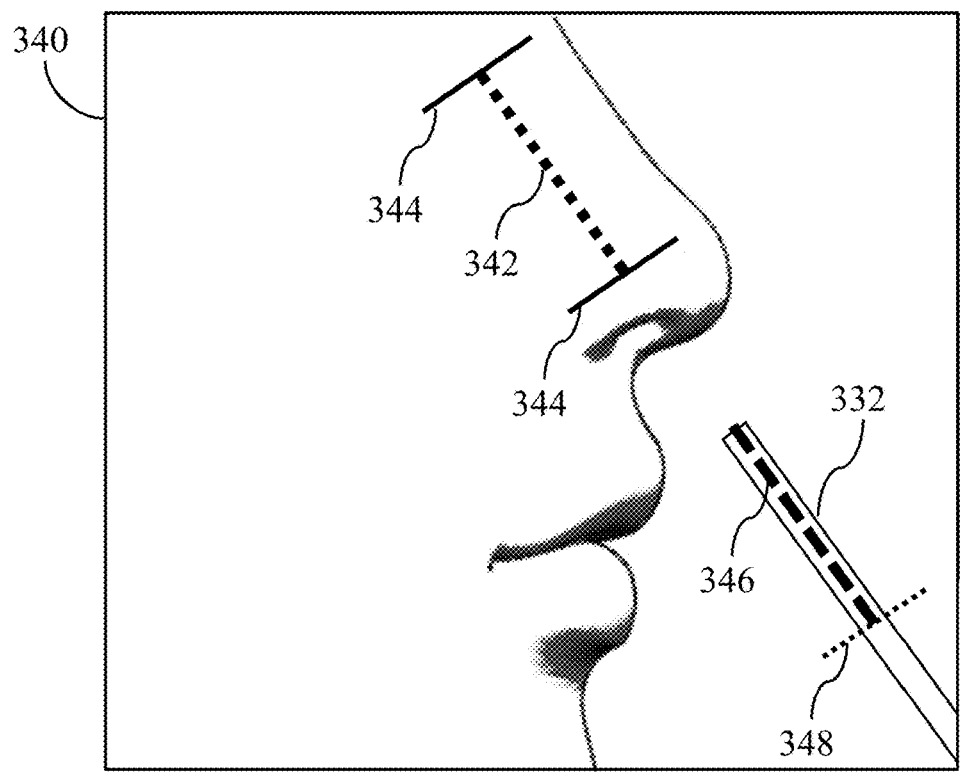
Figure 6C:
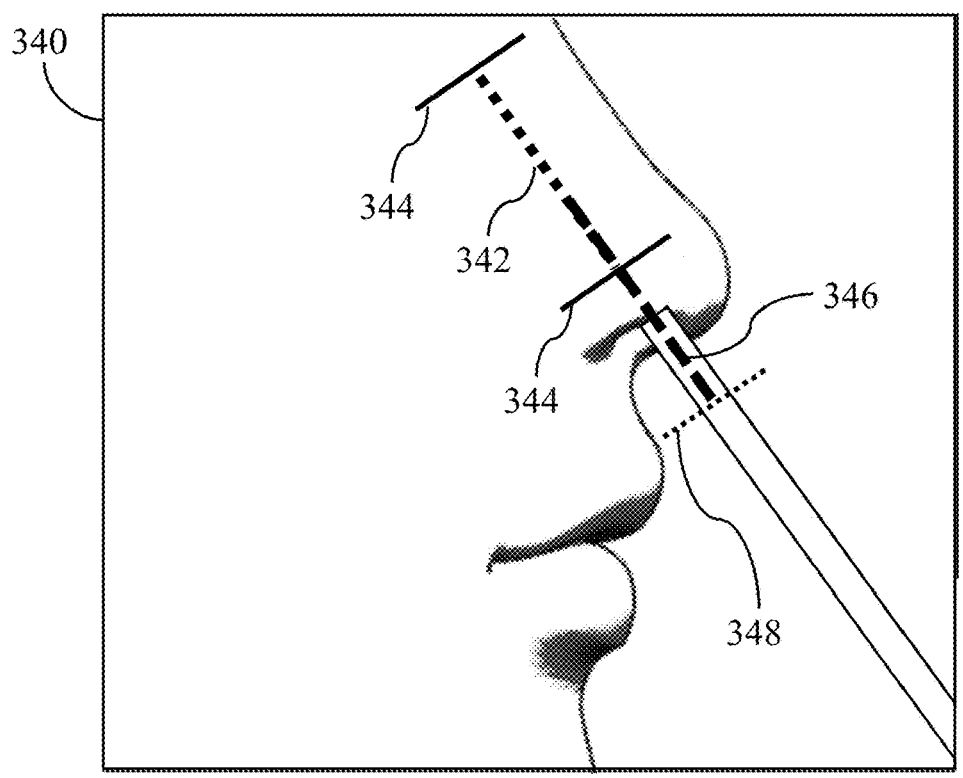
Figure 6D:
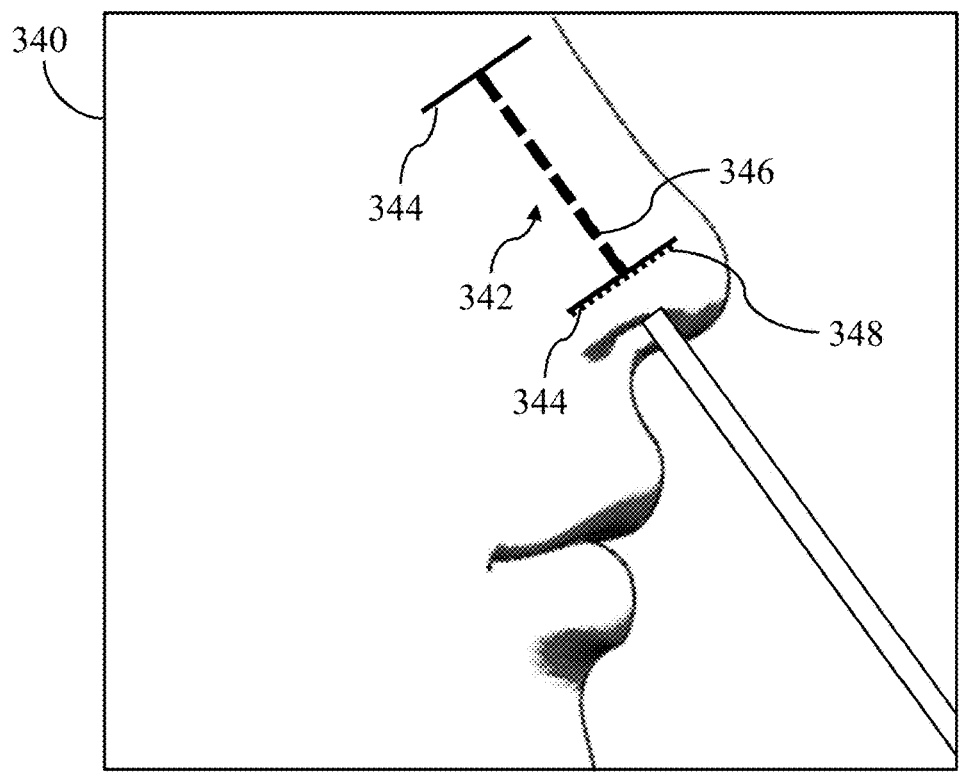

Images are captured (302) via the endoscope, and where the endoscope (100) is positioned with a view of the exterior of the nose the physical mark may be identified (304) using an object recognition, object detection, or other machine vision feature. This may include analyzing captured images and detecting for a particular color associated with a colored marker, or a particular visual pattern or reflection associated with a sticker or other physical optical marker that is placed on the exterior of the nose. The system may also determine (306) a length of the implant tool (330) and the implant (336), which may include determining the length of the shaft (332), the implant (336), and the position of the implant (336) within or relative to the shaft (332). This determination may be made based upon pre-configured information associated with the procedure, or based upon a serial number/model number of the implant tool (330), or may be based upon the detection of visually distinct markings on the shaft (332) in images captured by the endoscope (100). As an example, the shaft (332) may have visually distinct colored markings along the shaft (332) to indicate the position of each end of the implant within the shaft (332) when fully extended.

Where the endoscope (100) is positioned at the exterior of the nose and a marking has been identified (304), the system may overlay (308) an implant boundary on each end of the marking. FIG. 6A illustrates an interface (340) that may be provided during procedure guidance through the above steps. The shaft (332) is shown within the captured image prior to insertion, and the marking (342) is shown on the exterior of the nose. FIG. 6B illustrates the interface (340) after identification (304) of the mark (342), and overlay (308) of the implant boundaries (344) relative to the mark (342). Where the determined (306) length of the shaft and/or implant do not match the length of the mark (342), the system may notify the user and/or automatically extend the overlaid (308) implant boundary to the determined length. The combination of the mark (342) and the implant boundaries (344) via the interface (340) serve as a visual guide to the intended position of the implant (336) upon successful deployment, such that the implant should align with the mark (342) and fall between the boundaries (344).

The system may also detect (316) the orientation of the implant tool shaft (332) using an object recognition process and/or identification of optical markers on the shaft (332) and/or body of the implant tool itself (330). As an example, this could include high visibility reflectors positioned along the shaft (332) and tool (330), which are readily detectable by an infrared light project and receiver or other optical locator, or that are readily detectable by an object recognition or other machine vision process applied to captured images. With the instrument orientation determined, the system may overlay (318) an implant marker on the instrument where the implant is located (e.g., within the shaft (332). This may be determined based upon the identified position and orientation of the instrument, the determined instrument and implant length, and other information, for example. Referring again to FIG. 6B, an implant marker (346) is shown overlaid upon the distal end of the shaft (332), at the position where the implant (336) rests within the shaft (332). An implant proximal end (348) is also visually indicated. In some implementations this may be a visual overlay to the interface (340) that is determined based upon determined position and orientation of the shaft, as well as known characteristics of the implant tool (330) and implant (336) (e.g., length and position of the implant (336) within the shaft (332). In some implementations, the implant proximal end (348) may also be indicated by a physical marking on the shaft (332) itself instead of or in addition to the marking overlaid on the interface (340).

With several markings identified and/or overlaid upon the interface (340), the system may continuously track and update such markers as additional images are captured by the endoscope (100), and may display subsequent images and updated markings as the positions of objects within the image change. As subsequent images are captured and markers are updated, the interface (340) will continuously show the projected target path or endpoint of the shaft (332) and implant (336) based upon detected (316) changes in orientation of the instrument, which will aid the surgeon in aligning and inserting the shaft (332) into the nasal wall in real time (e.g., where the projected target path of the shaft (332) does not align with the marker (342), the surgeon may reposition and/or reorient the shaft (332)).

A user of the implant tool (330) may insert the shaft (332) into the nasal wall and navigate it through the tissue of the nasal wall until the implant marker (346) is in alignment (320) with the exterior marker (342), and is inserted to a depth (322) at which the implant marker (346) is contained entirely within the implant boundaries (344). In some implementations the system may provide visual, audible, and/or haptic guidance to indicate when proper alignment (320) and depth (322) have been achieved, and/or may provide visual, audible, and/or haptic guidance to indicate (324) when a full deployment position has been achieved (e.g., both alignment and depth). In some implementations, the system may actuate a mechanical lock on the control (334) to allow deployment of the implant (336) only after indicating (324) the deployment position has been reached, or may automatically actuate the control (334) or otherwise retract the shaft (332) after indicating (324) the deployment position has been reached.

Where the implant tool (330) is a separate system or device from the endoscopic guidance system of FIG. 1, such automation may be accomplished via wireless and/or wired communication between the system, such as a Bluetooth transmission from the image processor (104) to the implant tool (330) or its control system that indicates the deployment position has been reached, or an audible tone from the image processor (104) that is detected by a microphone of the implant tool (330), for example.

Figure 7:
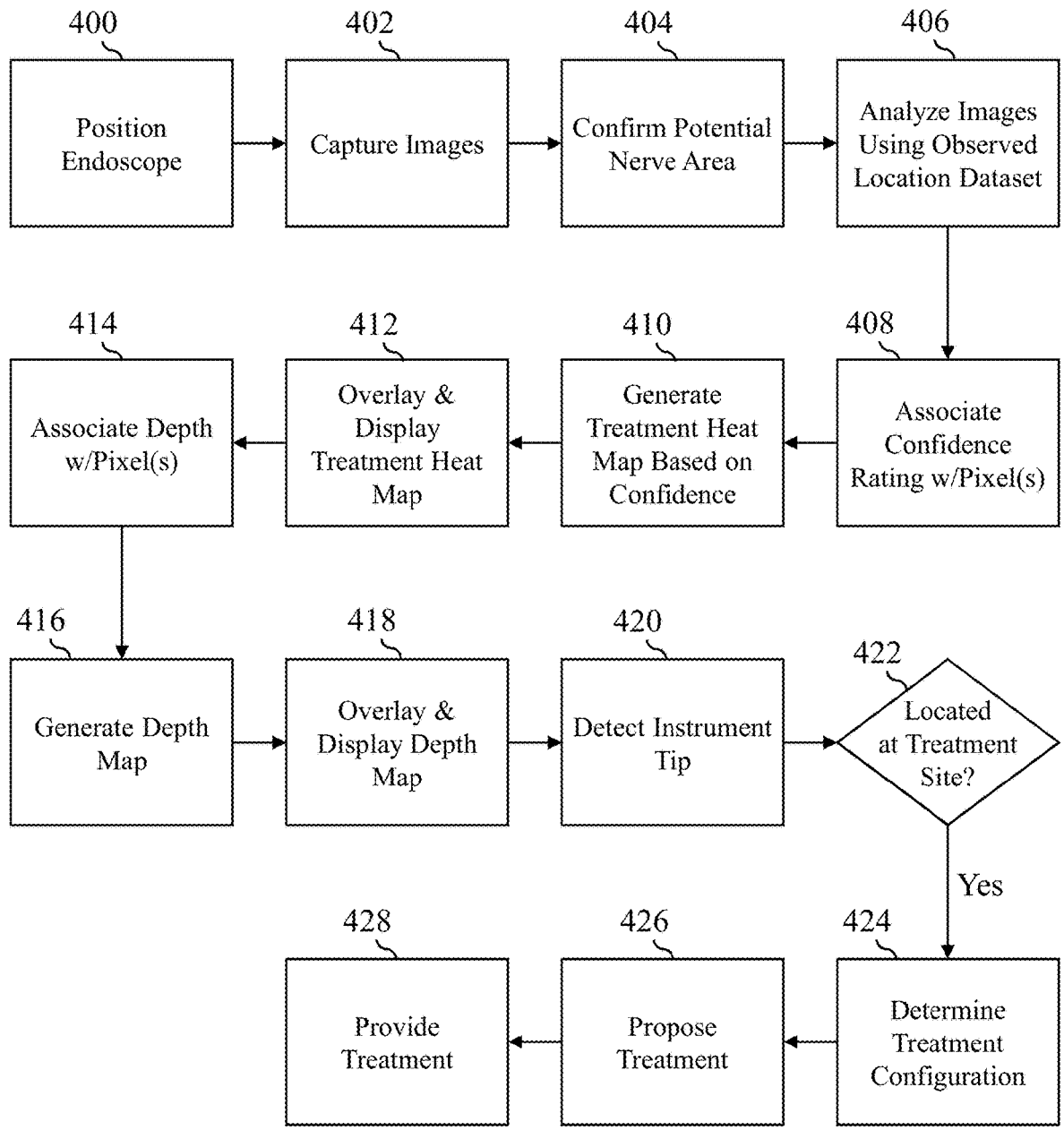
FIG. 7 is a flowchart of an exemplary set of steps that may be performed to provide procedure guidance during treatment of nerves embedded within tissue.

During treatment of nerves, such as ablation to treat chronic pain or other conditions, in can be difficult to accurately identify the locations of nerve structures since they are obscured by tissue, and their particular structure and location can be different from patient to patient. FIG. 7 is a flowchart of an exemplary set of steps that may be performed to provide procedure guidance during treatment of nerves embedded within tissue, and to aid in identifying the likely locations of nerves within the tissue. As with other procedure guidance, the endoscope may be positioned (400) to view patient anatomy in the generalized area where the target nerves are located, and images are captured (402).

In some implementations, the system may analyze captured images to confirm (404) that they depict the generalized area where the nerves will be located, which may include using an object recognition or other machine vision process, which itself may be configured and/or trained using sets of input images and paired labels or annotations, as has been previously described.

The system may analyze (406) images captured of the generalized nerve area using an object recognition or other machine vision process that is configured or trained based upon an observed location dataset. The observed location dataset includes a plurality of images of the generalize nerve area captured from other procedures, and such images are paired with labels, annotations, or other data that describes the actual measured or determined position of the nerves for each image that depicts exterior tissue that covers the nerves.

As an example, the observed location dataset may be created by capturing endoscopic images of the generalized area where a particular nerve (e.g., the posterior nasal nerve, or "PNN") will be located within a number (e.g., between about 500 and about 100) of cadaveric samples. The cadaveric samples may then be dissected and/or further studied to determine the precise location of nerve tissue such as the PNN for that sample, and information describing this precise location may be associated with each image captured of that cadaveric sample. This associations may be expressed using absolute or relative measurements and/or coordinate systems indicating, for each image, the precise location of the PNN within that image (e.g., an X and Y position, as well as a Z position or depth below the tissue, or relative to the image capture perspective).

Figure 8A:
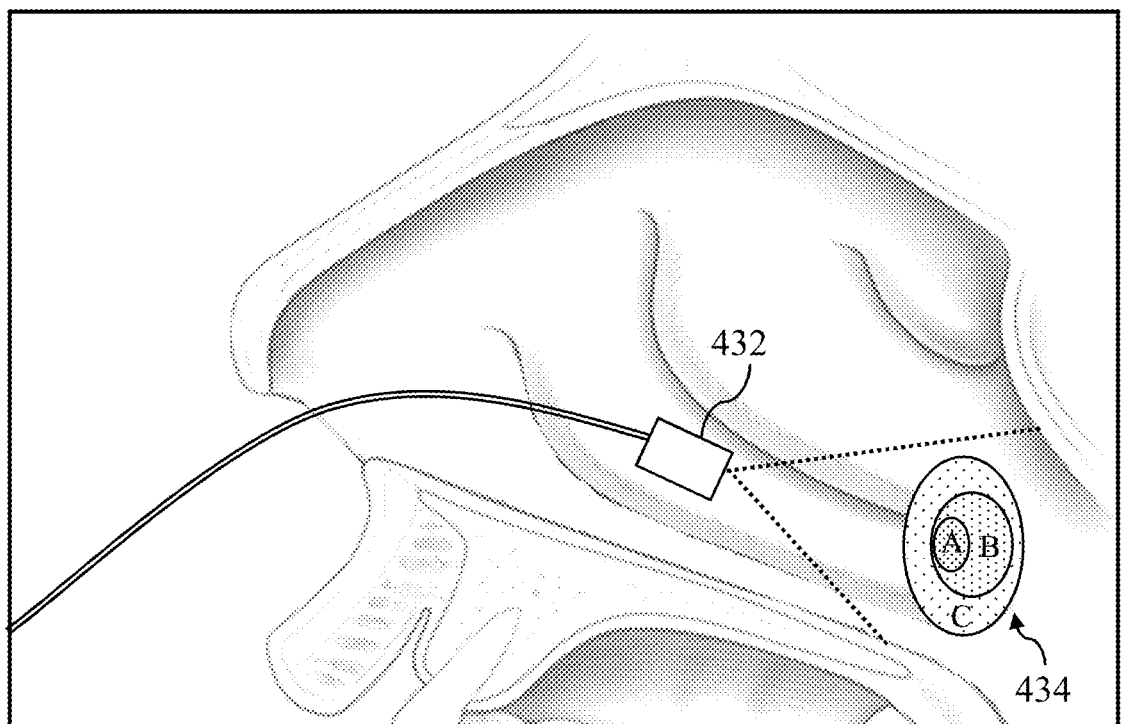
FIG. 8A-8C illustrate exemplary interfaces that may be provided during procedure guidance such as that described in FIG. 7.
Figure 8B:
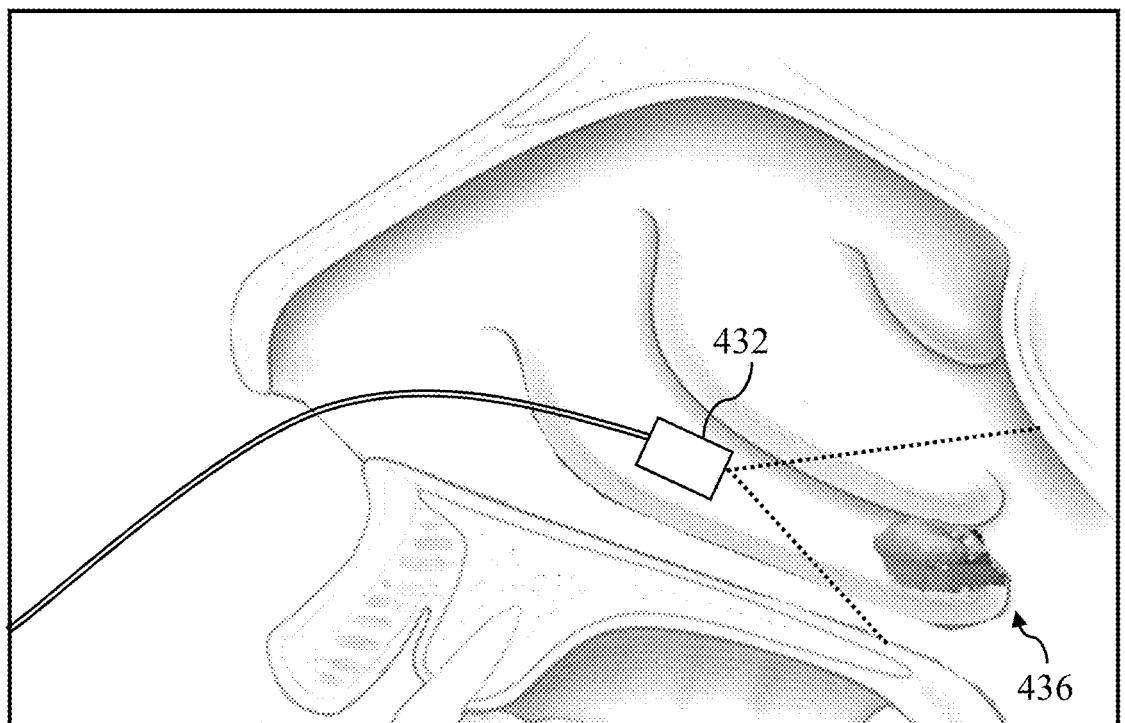

An image recognition process that is configured or trained based upon this observed location dataset may then analyze images captured (402) during the guided procedure for similarities to the dataset images, and then may estimate the position and depth of the nerve tissue within the captured (402) images based upon this analysis. The system may then associate (408) a confidence rating, score, value, or other data expressing a likelihood of nerve tissue being present with each pixel or pixel grouping (e.g., a number of proximate or contiguous pixels) to determine one or more sub-areas within the generalized area where the nerve tissue is likely to be located. The system may then generate (410) a treatment heatmap based on the pixel confidence ratings, and may overlay (412) and display the treatment heatmap via an interface such as that illustrated in FIGS. 8A-8C. While the interface (430) illustrated in those figures is shown as a cross-sectional view of the nasal cavity for clarity and ease of illustration, it should be understood that the actual interface and captured endoscopic images would be from the perspective of an endoscope within the nasal canal, rather than a cross-sectional view.

The illustrated interface (430) is captured from the perspective of an endoscope (432) positioned within the nasal cavity, and directed towards the generalized location of the PNN. A heatmap (434) is shown overlaid upon the illustrated interface (430), which may be observable as an overlay upon endoscopic images captured by the endoscope (432). As can be seen, the heatmap (434) includes several different sections or zones, each having a distinct visual appearance such as a color, pattern, size, shape, or other characteristic. The zone marked "A" covers a small area and is associated with a first pattern indicating a moderate-high likelihood of containing the PNN nerves, the zone marked "B" covers a somewhat larger area that includes zone A, and is associated with a second pattern indicating a high likelihood of containing the PNN nerves, and the zone marked "C" covers an even larger area that includes both prior zones, and that is associated with a third pattern indicating a very high likelihood of containing the PNN nerves.

As an example of the above, the heatmap (434) might indicate that zone A is 80% likely to entirely contain the PNN, zone B is 90% likely to entirely contain the PNN, and zone C is 99% likely to entirely contain the PNN. The size, shape, position, and confidence estimates for each zone may be based upon data such as statistical histograms and image correlations between the captured (402) images and those of the observed location dataset, as has been previously described. A surgeon may use the heatmap (434) to guide treatment decisions, such as the type of ablation device or operational characteristics that are used (e.g., ablation to a wide area vs. a narrow area), the locations where energy is provided during ablation, and the magnitude of energy provided during ablation. Following the above example, where a surgeon desired a conservative approach to ablation, energy delivery may be confined to zone A in the understanding that it is likely to be effective, but that some additional treatment may be needed. Conversely, where the surgeon prioritizes success of the first treatment over other factors (e.g., patient comfort), energy delivery may instead be confined to zone C in the understanding that it will almost assuredly be effective, but that additional collateral tissue may also be ablated.

In some implementations, the system may also associate (414) the depth of nerve tissue with pixels or pixel groupings in the captured images based upon the observed location dataset analysis (406), and may generate (416) a depth map for the captured images based upon the pixel-depth associations. This depth map may be overlaid (418) on the illustrated interface and displayed, as illustrated by the depth map (436) shown in FIG. 8B. The interface (430) may display the heatmap (434), depth map (436), or both, and may be selectively switched between as desired by a user.

Figure 8C:
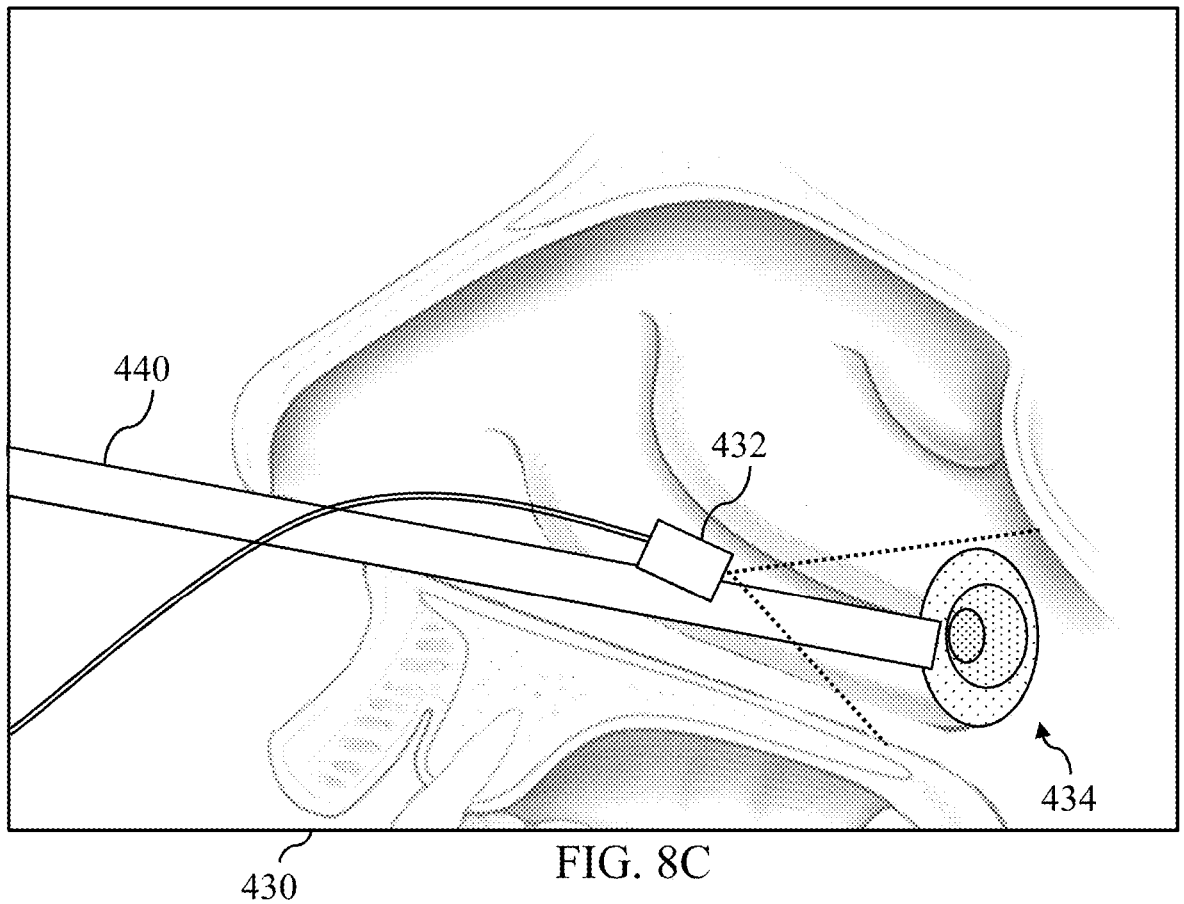

After the treatment plan has been decided, an ablation instrument (440) may be navigated to the procedure site while the endoscope (432) continues to capture images, as illustrated in FIG. 8C. The system may detect (420) the ablation instrument (440) tip in the captured images, and may begin to track and/or visually indicate the location of the detected tip, as has been previously described. When the distal tip of the instrument (440) is detected proximal to or in contact with tissue associated with the heatmap (434), the system may determine (422) that the instrument is positioned at the treatment site, and may determine (424) and propose (426) a set of treatment configurations to the user via the interface (430). Treatment configurations may include, for example, the direction and scope of energy delivery (e.g., wide or narrow) determined based on the heatmap (434) and underlying data, or the length and magnitude of energy delivery (e.g., shallow or deep delivery) determined based on the depth map (436) and underlying data.

The proposed (426) treatment configuration may be manually adjusted and/or accepted by the surgeon, and then the treatment may be provided (428) by activation of the ablation instrument (440). As with prior examples, where the endoscope guidance system of FIG. 1 is separate from the ablation instrument (440) system, information relating to treatment configurations and locations relative to the treatment site may be communicated via wireless or wired communication between the two systems, such as by communication over a Bluetooth interface to transmit proposed (426) treatment configurations to an energy generator coupled to the ablation instrument (440).

Another example of procedure guidance that may be provided by the system is landmark based guidance for navigating an endoscope to the location of, and identification of, patient anatomy that is obscured and/or difficult to identify even when viewed. As an example, the Eustachian Tube, or "ET" is deep within the nasal cavity, which presents a challenge for diagnostic and treatment procedures that involve navigating an endoscope or other instruments to the opening of the Eustachian Tube. Even when viewed from a proximal endoscope, the ET is difficult to locate with high confidence because tissue covers the ET well at the posterior (e.g., around 1 cm past the inferior turbinate).

Figure 9:
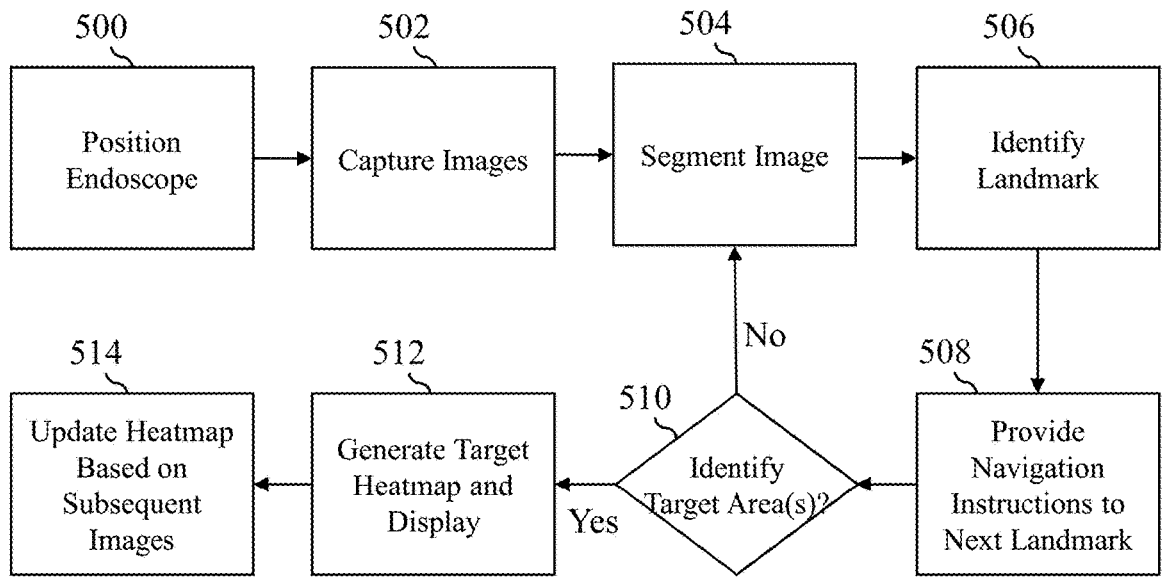
FIG. 9 is a flowchart of an exemplary set of steps that may be performed to provide procedure guidance during navigation of a surgical instrument to visually obstructed anatomy.

FIG. 9 is a flowchart of an exemplary set of steps that may be performed to provide procedure guidance during navigation of a surgical instrument to visually obstructed or difficult to locate anatomy, such as the ET. As with other procedure guidance, the endoscope (100) may be positioned (500) with a field of view directed towards the depths of the nasal cavity. Images are captured (502) by the endoscope (100), and are segmented (504) to determine the depth and/or scale of portions of the captured (502) images. This may include determining depth based upon the visual appearance of tissue illuminated by a known light source such as an LED at the tip of the endoscope (100) and analysis by an expert system or artificial intelligence system that is configured and/or trained to determine depth based upon two-dimensional images, or may include determining depth and/or scale based upon a projected laser focal point, patterned light, or other optical marker that has a predictable appearance that is determined based on the distance and surface that it is projected onto.

The system may identify (506) one or more anatomical landmarks based upon the two dimensional appearance of the landmarks in the captured (502), as well as upon the spatial characteristics of, and/or spatial relationships between, the targeted anatomical landmarks based upon the segmentation data. The system may then provide (508) navigation instructions via a software interface displayed on the image processor (104) or another device, which may be followed by the surgeon (e.g., by navigating the endoscope (100)) in order to move from the identified (508) landmark to a determined or suspected position of a subsequent anatomical landmark. Subsequent landmarks may be identified (506) based on subsequent images captured during navigation, and additional navigation instructions may be provided (508), until the target area (e.g., the destination anatomy) is identified (510).

Figure 10:
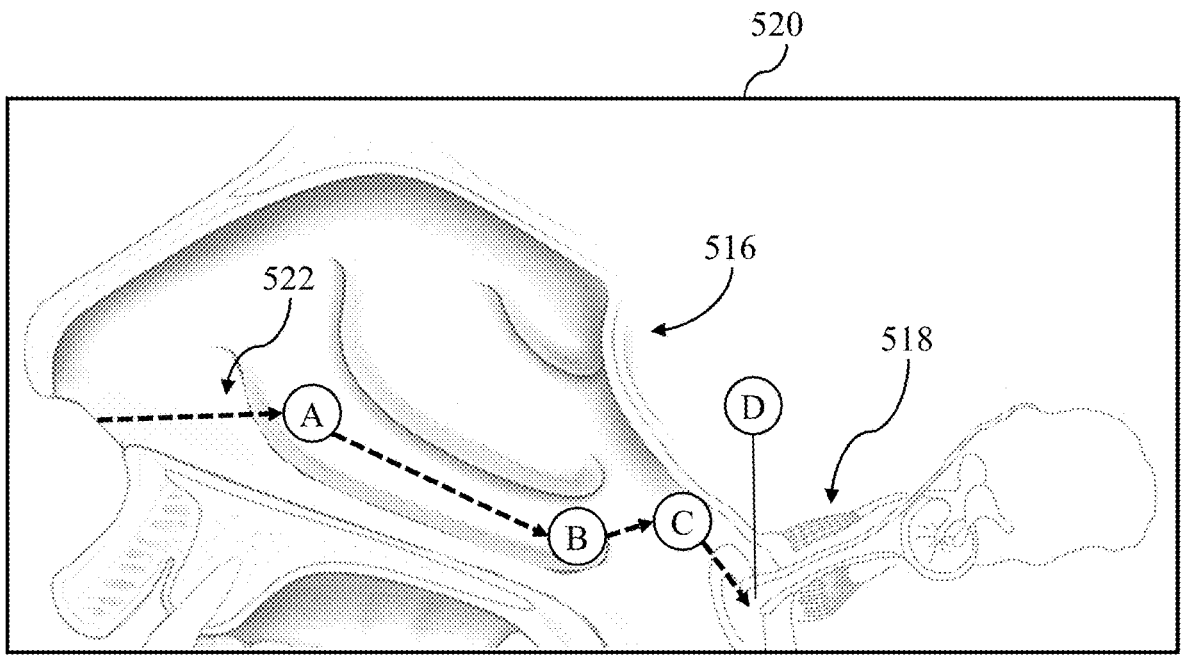
FIG. 10 illustrates an exemplary interface that may be provided during procedure guidance such as that described in FIG. 9.

FIG. 10 illustrates an exemplary interface (520) that may be provided during procedure guidance such as that described in FIG. 9. As with prior examples, the interface (520) is illustrated by way of a cross sectional view of the nasal canal for the sake of clarity, and it should be understood that the interface (520) that is displayed via the image processor (104) or another device would include images captured from the perspective of an endoscope navigating the nasal canal rather than a cross section. The illustrated interface (520) would display, throughout navigation, a sequence of captured endoscopic images with navigation markers plotting a path along one or more anatomical milestones to the target area (e.g., the opening of the ET). The navigation path (522) is illustrated as a set of dotted lines connecting navigation milestones labeled A through C, with the target anatomy being labeled D. The navigation path (522) originates at the opening of the nasal canal (516), passes through the nasal canal (516), and terminates at the opening to the ET (518).

As an example of the above, upon insertion of the endoscope (100) into the nasal canal (516) the interface (520) may display captured images, and may visually indicate the approximate position of milestone A (e.g., a proximal portion of the inferior turbinate). As the endoscope (100) is navigated to milestone A, an image will be captured in which milestone A will be identified (506) by the system with confidence. As with prior examples, this may include use of an object recognition feature that is configured and/or trained with image datasets, labels, and annotations from other procedures, and that is capable of identifying similar visual characteristics between the presently captured (502) images and verified past images of the milestone anatomy.

After milestone A is identified (506), the system may provide (508) navigation instructions for reaching milestone B (e.g., a distal portion of the inferior turbinate), which may take the form of a visual indication overlaid upon captured images at the approximate position of milestone B. As the endoscope is navigated towards milestone B based on the visual indicator, an image will be captured in which milestone B will be identified (506), and the system may then provide (508) instructions indicating the approximate position of milestone C (e.g., a wall of the nasopharynx just opposite the distal portion of the inferior turbinate). After milestone C is positively identified (506), the system may then provide (508) instructions indicating the approximate position of the destination D (e.g., the opening to the ET). As will be apparent, additional milestones may exist and may be used beyond those shown in FIG. 10, and for example may include additional milestones along the inferior turbinate, within the nasopharynx, or otherwise.

As the endoscope (100) is navigated within view of the destination D, the system will identify the target anatomy (510) and provide an indication of the location of the target anatomy within the captured image displayed via the interface (520). This may include any type of visually distinct marker or indicator. Where identification of the target anatomy is not possible to a high degree of confidence, the system may instead overlay a heatmap style visual indicator, as described above in the context of FIG. 8A.

In such an implementation, the system may generate (512) a target heatmap and display the heatmap via the interface (520), and then may continuously update (514) the heatmap as the endoscope (100) is navigated closer to the indicated area. Continuing the above example, upon navigating from milestone C towards destination D, the system may identify the generalized area of the ET opening, and may overlay a heatmap indicating areas within the generalized area that the ET is likely to be (e.g., 99% confidence it is within a larger patterned zone, 80% confidence it is within a smaller patterned zone). As navigation continues towards one of the marked zones, additional images may be captured with a different perspective and/or lighting, and the system may update (514) and redisplay the heatmap based upon the improved visual conditions (e.g., the smallest marked zone may have a confidence of 99% or higher, indicating with a high degree of confidence the location of the ET opening).

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. An endoscope system with procedure guidance comprising:
   (a) an endoscope configured to capture image data;
   (b) one or more processors configured to receive image data and provide procedure guidance via a display based on a procedure type;
   (c) a machine vision function configured to be executed by the one or more processors to identify characteristics of captured image data;
   (d) a memory configured to store, for each of a plurality of procedure types, a set of procedure events, wherein the set of procedure events is usable by the one or more processors to identify the occurrence of particular events during the corresponding procedure type;
   wherein the one or more processors are configured to:
   (i) initiate a procedure in response to receiving a selection indicating the procedure type and, during the procedure, receive a set of image data and a set of procedure data, and cause an interface to appear via the display, wherein the interface comprises an endoscope view based on the set of image data;
   (ii) using the machine vision function and based on the procedure type, identify a position of a distal tip of a surgical instrument associated with that procedure type within a first image of the set of image data, and continue to track the position of the distal tip within subsequent images of the set of image data;
   (iii) based on the set of procedure events for the procedure type and the set of procedure data, identify the occurrence of an event; and
   (iv) in response to identifying the occurrence of the event, update the interface to position an event overlay on the endoscope view based on the position of the distal tip and an event type of the event, and cause the updated interface to appear on the display.

2. The endoscope system of claim 1, wherein the event is associated with energy delivery via the distal tip, the set of procedure data describes characteristics of energy delivery via the distal tip, and the machine vision function is configured to identify an energy delivery contact within the set of image data as the distal tip.

3. The endoscope system of claim 2, wherein the one or more processors are further configured to, when updating the interface to position the overlay on the endoscope view:
   (i) based on the position of the distal tip at the time of occurrence of the event, identify a portion of patient anatomy depicted within the endoscope view at which energy deliver occurred; and
   (ii) position the event overlay at the portion of patient anatomy, wherein the event overlay comprises a visual indicator of energy delivery.

4. The endoscope system of claim 3, wherein the set of procedure data comprises an energy delivery time that describes a time period over which energy was delivered, and an energy delivery magnitude describing a magnitude of energy delivery during moments of the energy delivery time, wherein the one or more processors are further configured to determine one or more visual characteristics of the visual indicator of energy delivery based on the energy delivery time and the energy delivery magnitude.

5. The endoscope system of claim 3, wherein the one or more processors are further configured to:
   (i) based on the set of procedure events for the procedure type and the set of procedure data, identify the occurrence of a plurality of energy delivery events; and
   (ii) in response to identifying the occurrence of the plurality of energy delivery events, update the interface to position a plurality of event overlays on the endoscope view based on the position of the distal tip corresponding to each of the plurality of energy delivery events, and cause the updated interface to appear on the display.

6. The endoscope system of claim 3, wherein the one or more processors are further configured to:
   (i) identify a position of a diagnostic tip of a diagnostic instrument within a second image of the set of image data, and continue to track the position of the diagnostic tip within subsequent images of the set of image data;
   (ii) receive a diagnostic signal from the diagnostic instrument, wherein the diagnostic signal comprises an indication of energy delivery to patient anatomy;
   (iii) in response to receiving the diagnostic signal, determine the portion of patient anatomy that corresponds to the diagnostic signal based on the position of the diagnostic tip; and
   (iv) update the visual indicator that corresponds to the portion of patient anatomy to indicate success or failure based on the indication of energy delivery.

7. The endoscope system of claim 1, wherein the one or more processors are further configured to, when identifying the position of the distal tip:
   (i) determine a three-dimensional position of the distal tip within a three-dimensional system based on the endoscope view, relative to a perspective from which the set of image data was captured; and
   (ii) determine a three-dimensional orientation of the distal tip within the three-dimensional system, relative to the perspective from which the set of image data was captured.

8. The endoscope system of claim 7, wherein the one or more processors are further configured to:
   (i) when updating the interface to position the event overlay on the endoscope view, position the event overlay on the endoscope view based on the three-dimensional position of the distal tip; and
   (ii) determine a change in the perspective of the endoscope view, and update the interface to reposition the event overlay on the endoscope view based on the change in the perspective and the three-dimensional system.

9. The endoscope system of claim 1, wherein the event is associated with implantation of an implant via the distal tip of an implant tool, and the set of procedure data describes lengths of the implant and the implant tool, and the machine vision function is configured to identify a longitudinal marking on an exterior of a patient's nose, wherein the one or more processors are further configured to:
   (i) identify the occurrence of the event based on identification of the longitudinal marking and the distal tip; and
   (ii) update the interface to position the event overlay based on the position of the longitudinal marking, the lengths of the implant and the implant tool, and the position of the distal tip.

10. The endoscope system of claim 9, wherein the event overlay comprises:
    (i) an implant boundary positioned based on the position of the longitudinal marking and the lengths of the implant and the implant tool; and (ii) an implant marker positioned based on the position of the distal tip.

11. The endoscope system of claim 10, wherein the one or more processors are further configured to:
(i) determine, based on the positions of the longitudinal marking, the implant boundary, and the implant marker, when the implant marker is aligned within the longitudinal marking and within the implant boundary; and
(ii) in response, provide an indication that the implant is positioned at a deployment position.

12. A method for endoscope procedure guidance comprising, by one or more processors of an endoscope system:
(a) storing a machine vision function configured to be executed by the one or more processors to identify characteristics of captured image data;
(b) storing, for each of a plurality of procedure types, a set of procedure events, wherein the set of procedure events is usable by the one or more processors to identify the occurrence of particular events during the corresponding procedure type;
(c) initiating a procedure in response to receiving a selection indicating the procedure type and, during the procedure, receiving a set of image data from an endoscope, receiving a set of procedure data, and causing an interface to appear via a display of the endoscope system, wherein the interface comprises an endoscope view based on the set of image data;
(d) using the machine vision function and based on the procedure type, identifying a position of a distal tip of a surgical instrument associated with that procedure type within a first image of the set of image data, and continuing to track the position of the distal tip within subsequent images of the set of image data;
(e) based on the set of procedure events for the procedure type and the set of procedure data, identifying the occurrence of an event; and
(iv) in response to identifying the occurrence of the event, updating the interface to position an event overlay on the endoscope view based on the position of the distal tip and an event type of the event, and causing the updated interface to appear on the display.

13. The method of claim 12, wherein the event is associated with energy delivery via the distal tip, the set of procedure data describes characteristics of energy delivery via the distal tip, and the machine vision function is configured to identify an energy delivery contact within the set of image data as the distal tip.

14. The method of claim 13, further comprising, when updating the interface to position the overlay on the endoscope view:
(i) based on the position of the distal tip at the time of occurrence of the event, identifying a portion of patient anatomy depicted within the endoscope view at which energy deliver occurred; and
(ii) positioning the event overlay at the portion of patient anatomy, wherein the event overlay comprises a visual indicator of energy delivery.

15. The method claim 14, wherein the set of procedure data comprises an energy delivery time that describes a time period over which energy was delivered, and an energy delivery magnitude describing a magnitude of energy delivery during moments of the energy delivery time, further comprising determining one or more visual characteristics of the visual indicator of energy delivery based on the energy delivery time and the energy delivery magnitude.

16. The method of claim 14, further comprising:
(i) based on the set of procedure events for the procedure type and the set of procedure data, identifying the occurrence of a plurality of energy delivery events; and
(ii) in response to identifying the occurrence of the plurality of energy delivery events, updating the interface to position a plurality of event overlays on the endoscope view based on the position of the distal tip corresponding to each of the plurality of energy delivery events, and causing the updated interface to appear on the display.

17. The method of claim 14, further comprising:
(i) identifying a position of a diagnostic tip of a diagnostic instrument within a second image of the set of image data, and continuing to track the position of the diagnostic tip within subsequent images of the set of image data;
(ii) receiving a diagnostic signal from the diagnostic instrument, wherein the diagnostic signal comprises an indication of energy delivery to patient anatomy;
(iii) in response to receiving the diagnostic signal, determining the portion of patient anatomy that corresponds to the diagnostic signal based on the position of the diagnostic tip; and
(iv) updating the visual indicator that corresponds to the portion of patient anatomy to indicate success or failure based on the indication of energy delivery.

18. The method of claim 12, further comprising, when identifying the position of the distal tip:
(i) determining a three-dimensional position of the distal tip within a three-dimensional system based on the endoscope view, relative to a perspective from which the set of image data was captured; and
(ii) determining a three-dimensional orientation of the distal tip within the three-dimensional system, relative to the perspective from which the set of image data was captured.

19. The method of claim 18, further comprising:
(i) when updating the interface to position the event overlay on the endoscope view, positioning the event overlay on the endoscope view based on the three-dimensional position of the distal tip; and
(ii) determining a change in the perspective of the endoscope view, and updating the interface to reposition the event overlay on the endoscope view based on the change in the perspective and the three-dimensional system.

20. The method of claim 12, wherein the event is associated with implantation of an implant via the distal tip of an implant tool, and the set of procedure data describes lengths of the implant and the implant tool, and the machine vision function is configured to identify a longitudinal marking on an exterior of a patient's nose, the method further comprising:
(i) identifying the occurrence of the event based on identification of the longitudinal marking and the distal tip;
(ii) updating the interface to position the event overlay based on the position of the longitudinal marking, the lengths of the implant and the implant tool, and the position of the distal tip, wherein the event overlay comprises an implant boundary positioned based on the position of the longitudinal marking and the lengths of the implant and the implant tool, and an implant marker positioned based on the position of the distal tip;
(iii) determining, based on the positions of the longitudinal marking, the implant boundary, and the implant marker, when the implant marker is aligned within the longitudinal marking and within the implant boundary; and (iv) in response, providing an indication that the implant is positioned at a deployment position.

* * * * *